US012727842B2

(12) United States Patent
Hernandez Barron et al.

(10) Patent No.: US 12,727,842 B2
(45) Date of Patent: Sep. 8, 2026

(54) FIDUCIALS DETECTION FOR MOVEMENT ESTIMATION AND GUIDANCE

(71) Applicant: GE Precision Healthcare LLC, Waukesha, WI (US)

(72) Inventors: Heber Alejandro Hernandez Barron, Salt Lake City, UT (US); Jon Thomas Lea, Salt Lake City, UT (US); Jordan Paul Brown, Woods Cross, UT (US); Rhianne Hsu, Salt Lake City, UT (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 147 days.

(21) Appl. No.: 18/905,519

(22) Filed: Oct. 3, 2024

(65) Prior Publication Data

US 2026/0096797 A1 Apr. 9, 2026

(51) Int. Cl.

*A61B 6/00* (2024.01)
*A61B 6/46* (2024.01)
*A61B 90/00* (2016.01)

(52) U.S. Cl.

CPC ............ *A61B 6/547* (2013.01); *A61B 6/4441* (2013.01); *A61B 6/463* (2013.01); *A61B 2090/3937* (2016.02)

(58) Field of Classification Search

CPC ....... A61B 6/547; A61B 6/4441; A61B 6/463; A61B 2090/3937

See application file for complete search history.

(56) References Cited

U.S. PATENT DOCUMENTS

| | | | | |
|---|---|---|---|---|
| 10,265,035 | B2 | 4/2019 | Fehre et al. | |
| 2016/0082596 | A1 | 3/2016 | Barth et al. | |
| 2021/0251591 | A1* | 8/2021 | Johnson | A61B 6/4441 |

OTHER PUBLICATIONS

Heemeyer et al., "Pose-aware C-Arm Calibration and Image Distortion Correction for Guidewire Tracking and Image Reconstruction", 2020 International Symposium on Medical Robotics (ISMR) Atlanta, GA, USA, Nov. 18-20, pp. 181-187. (Year: 2020).*
Esfandiari et al., "A Robust, Accurate and Low Cost C-Arm Base-Tracking System," 2015, CAOS International, 6 pgs.
Haliburton et al., "A Visual Odometry Base-Tracking System for Intraoperative C-Arm Guidance," 20 pgs.
Haliburton et al., "A Clinical C-Arm Base-Tracking System Using Computer Vision for Intraoperative Guidance," 2015, 134 pgs.

* cited by examiner

*Primary Examiner* — Kiho Kim
(74) *Attorney, Agent, or Firm* — Fletcher Yoder, P.C.

(57) ABSTRACT

An X-ray imaging system includes an X-ray radiation source, an X-ray detector, and a C-arm having the X-ray radiation source disposed on a first end and the X-ray detector disposed on a second end opposite the first end. The X-ray imaging system is configured to translate the C-arm in multiple different directions and to rotate the C-arm about multiple different axes. The X-ray imaging system includes an optical camera configured to capture image data of a position of the C-arm relative to a location. The X-ray imaging system includes a controller configured to receive the image data from the optical camera and to utilize machine vision both to determine an initial position of the C-arm relative to the location and to navigate a return of the C-arm to the initial position when the C-arm has been moved from the initial position based on the image data.

20 Claims, 11 Drawing Sheets

Degrees of Freedom

| | Motion Type |
|---|---|
| **Floor** | |
| 1. Push Forward/Back | Translation |
| 2. Push Side to Side | Translation |
| 3. Steering | Rotation |
| **Gantry Support** | |
| 4. Cross Arm In/Out | Translation |
| 5. Lift Column Up/Down | Translation |
| **Gantry** | |
| 6. Orbital (LAO/RAO) | Rotation |
| 7. Lateral (CRA/CAU) | Rotation |
| **Detector** | |
| 8. Digital Image Rotate | Rotation |

FIDUCIALS DETECTION FOR MOVEMENT ESTIMATION AND GUIDANCE

BACKGROUND

The subject matter disclosed herein relates to X-ray imaging systems and, more particularly, to fiducials detection for movement estimation and guidance for an X-ray imaging system having a C-arm.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned.

A common step in a surgical procedure is to use the mobile C-arm for some initial work and then move it away. Later in a surgical procedure, the mobile C-arm needs to be moved back to the same position where it was before it was moved to continue the surgery with assistance from the mobile C-arm. Returning to the same position can be a relatively time-consuming process that involves trial and error and taking some additional X-ray shots with the mobile C-arm to ensure that the mobile C-arm has been returned to the same position.

An extension of the issue of returning the mobile C-arm to the same position is the surgical step of taking a fluoroscopy shot at the start of the case and using that to set a baseline relative to the patient's body. Based on the starting position, more X-ray shots using the mobile C-arm while repositioning the mobile C-arm to align with a target anatomy of interest. This fluoro-hunting step is time-consuming process that uses X-rays to find the anatomy of interest and exposes patient to potentially unnecessary radiation.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with an embodiment, an X-ray imaging system is provided. The X-ray imaging includes an X-ray radiation source. The X-ray imaging system also includes an X-ray detector. The X-ray imaging system further includes a C-arm having the X-ray radiation source disposed on a first end and the X-ray detector disposed on a second end opposite the first end. The X-ray imaging system is configured to translate the C-arm in multiple different directions and to rotate the C-arm about multiple different axes. The X-ray imaging system further includes an optical camera configured to capture image data of a position of the C-arm relative to a location. The X-ray imaging system further includes a controller including a memory and a processing system including one or more processors, and the controller is configured to receive the image data from the optical camera and to utilize machine vision both to determine an initial position of the C-arm relative to the location and to navigate a return of the C-arm to the initial position when the C-arm has been moved from the initial position based on the image data.

In accordance with another embodiment, a computer-implemented method is provided. The computer-implemented method includes receiving, at a processing system including one or more processors, image data from an optical camera mounted on a C-arm of an X-ray imaging system. The X-ray imaging system includes an X-ray radiation source, an X-ray detector, and the C-arm having the X-ray radiation source disposed on a first end and the X-ray detector disposed on a second end opposite the first end. The X-ray imaging system is configured to translate the C-arm in multiple different directions and to rotate the C-arm about multiple different axes. The optical camera is configured to capture image data of a position of the C-arm relative to a location. The computer-implemented method also includes utilizing, via the processing system, machine vision both to determine an initial position of the C-arm relative to the location and to navigate a return of the C-arm to the initial position when the C-arm has been moved from the initial position based on the image data.

In a further embodiment, a non-transitory computer-readable medium is provided. The non-transitory computer-readable medium includes processor-executable code that when executed by a processing system including one or more processors, causes the processing system to perform actions. The actions include receiving image data from an optical camera mounted on a C-arm of an X-ray imaging system. The X-ray imaging system includes an X-ray radiation source, an X-ray detector, and the C-arm having the X-ray radiation source disposed on a first end and the X-ray detector disposed on a second end opposite the first end. The X-ray imaging system is configured to translate the C-arm in multiple different directions and to rotate the C-arm about multiple different axes. The optical camera is configured to capture image data of a position of the C-arm relative to a location. The actions also include utilizing machine vision both to determine an initial position of the C-arm relative to the location and to navigate a return of the C-arm to the initial position when the C-arm has been moved from the initial position based on the image data.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
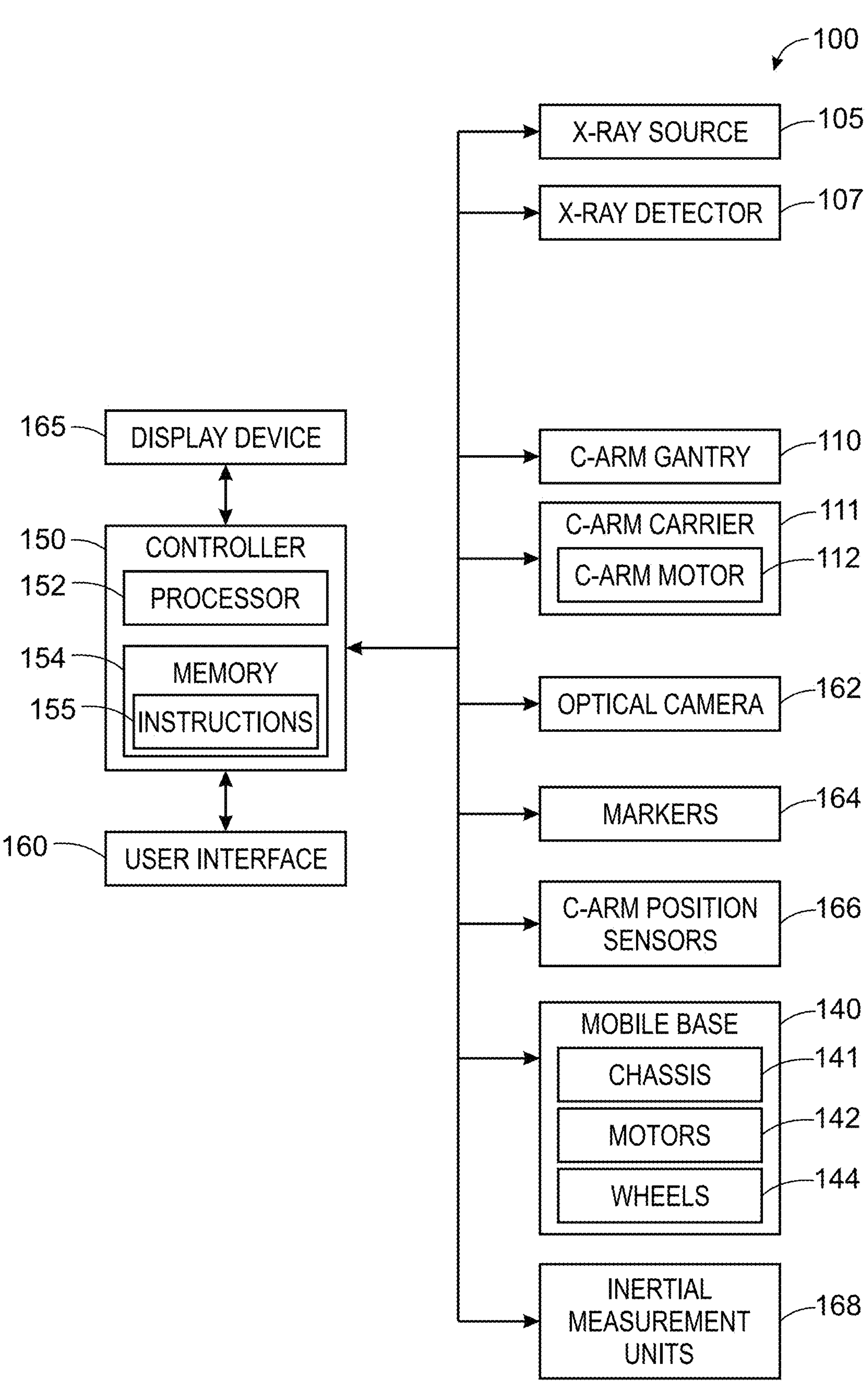
FIG. 1 is a block diagram illustrating components of an example X-ray imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure relates to systems and methods for fiducials detection for movement estimation and guidance for an X-ray imaging system having a C-arm. In particular, computer or machine vision based techniques (e.g., utilizing camera image data) to initially localize a C-arm and to utilize the same to realign, reposition, and/or reconfirm that the C-arm has reached (e.g., returned to) same location later (e.g., after having been moved) in an intraoperative setup or surgical procedure.

The disclosed systems and methods provide an easier and clearer way to return the C-arm to a previous (e.g., initial) position. The disclosed systems and methods may provide user instructions for the trajectory needed to be taken to return the C-arm to the previous position including, but not limited, to visual clues about where to go, how far, and what to check for correctness. These user aids can streamline the return to the same position workflow. The disclosed systems and methods could be utilized to virtually move an X-ray image to be virtually moved as the C-arm changes position to show the approximate place for the next X-ray shot. The disclosed systems and methods may eliminate the need for fluoro-hunting.

In the disclosed embodiments, an X-ray imaging includes an X-ray radiation source. The X-ray imaging system also includes an X-ray detector. The X-ray imaging system further includes a C-arm having the X-ray radiation source disposed on a first end and the X-ray detector disposed on a second end opposite the first end. The X-ray imaging system is configured to translate the C-arm in multiple different directions and to rotate the C-arm about multiple different axes. The X-ray imaging system further includes an optical camera configured to capture image data of a position of the C-arm relative to a location. The X-ray imaging system further includes a controller including a memory and a processing system including one or more processors, and the controller is configured to receive the image data from the optical camera and to utilize machine-vision both to determine an initial position of the C-arm relative to the location and to navigate a return of the C-arm to the initial position when the C-arm has been moved from the initial position based on the image data.

In certain embodiments, the optical camera is mounted on the C-arm (e.g., on X-ray detector or X-ray radiation source). In certain embodiments, the controller is configured to process initial image data received from the optical camera to identify images features, to enhance the image features that were identified, and to utilize the image features that were enhanced as reference features for returning the C-arm to the initial position. In certain embodiments, the controller is configured to receive an input from the user to activate utilization of the machine vision to navigate the return of the C-arm to the initial position. In certain embodiments, the controller is configured to process live image data received from the optical camera to identify subsequent image features, to enhance the subsequent image features that were identified, and to compare the subsequent image features that were enhanced to the reference features.

In certain embodiments, the X-ray imaging system includes a display, and wherein the controller is configured to cause display, on the display, of both the live image data along with user-perceptible instructions for navigating the C-arm back to the initial position based on the comparison of the subsequent image features that were enhanced to the reference features. In certain embodiments, the user-perceptible instructions include a direction of movement, a distance to a target, or a combination thereof. In certain embodiments, X-ray imaging system includes a display, and wherein the controller is configured to cause display, on the display, of both the live image data along with a reference image with the reference features to assist a user in navigating the C-arm back to the initial position. In certain embodiments, X-ray imaging system includes a display, and wherein the controller is configured to cause display, on the display, of the live image data, user-perceptible instructions for navigating the C-arm back to the initial position based on comparison of the subsequent image features that were enhanced to the reference features, and a reference image with the reference features to assist a user in navigating the C-arm back to the initial position.

In certain embodiments, the controller is configured to provide control signals to move (e.g., automatically) the C-arm and/or the X-ray imaging system to the initial position based on the comparison of the subsequent image features that were enhanced to the reference features. In certain embodiments, the initial image data and the live image data include red green blue images and/or depth images. In certain embodiments, the image features and the subsequent image features include sharp edges, significantly bright or dark areas, unique shapes or objects, and/or contrast information.

In certain embodiments, the X-ray imaging system includes a mobile base configured to move the X-ray imaging system, and the controller is configured, during movement of the X-ray imaging system via the mobile base from the initial position, to calculate a global localization of the C-arm and to map an environment based on the image data to form a trajectory relative to a floor that the mobile base is located on, and to utilize the trajectory in navigating the return of the C-arm to the initial position. In certain embodiments, the X-ray imaging system includes sensors disposed on components of the X-ray imaging system to determine a position and movement of the C-arm, and wherein the controller is configured to receive feedback from the sensors to determine a position and movement of the C-arm and to estimate movement of the mobile base. In certain embodiments, the sensors include one or more of a C-arm position sensor, an accelerometer, and a gyroscope. In certain embodiments, the X-ray imaging system includes one or more known markers disposed within a field of view of the optical camera, and the controller is configured to utilize the one or more known markers within the image data to determine respective positions of the X-ray imaging system and the C-arm relative to locations of the one or more known markers.

In the disclosed embodiments, a computer-implemented method includes receiving, at a processing system including one or more processors, image data from an optical camera mounted on a C-arm of an X-ray imaging system. The X-ray imaging system includes an X-ray radiation source, an X-ray detector, and the C-arm having the X-ray radiation source disposed on a first end and the X-ray detector disposed on a second end opposite the first end. The X-ray imaging system is configured to translate the C-arm in multiple different directions and to rotate the C-arm about multiple different axes. The optical camera is configured to capture image data of a position of the C-arm relative to a location. The computer-implemented method also includes utilizing, via the processing system, machine vision both to determine an initial position of the C-arm relative to the location and to navigate a return of the C-arm to the initial position when the C-arm has been moved from the initial position based on the image data.

In certain embodiments, the computer-implemented method further includes processing, via the processing system, initial image data received from the optical camera to identify images features, to enhance the image features that were identified, and to utilize the image features that were enhanced as reference features for returning the C-arm to the initial position. In certain embodiments, the computer-implemented method further includes receiving, at the processing system, an input from the user to activate utilization of the machine vision to navigate the return of the C-arm to the initial position and processing, via the processing system, live image data received from the optical camera to identify subsequent image features, to enhance the subsequent image features that were identified, and to compare the subsequent image features that were enhanced to the reference features.

In the disclosed embodiments, a non-transitory computer-readable medium includes processor-executable code that when executed by a processing system including one or more processors, causes the processing system to perform actions. The actions include receiving image data from an optical camera mounted on a C-arm of an X-ray imaging system. The X-ray imaging system includes an X-ray radiation source, an X-ray detector, and the C-arm having the X-ray radiation source disposed on a first end and the X-ray detector disposed on a second end opposite the first end. The X-ray imaging system is configured to translate the C-arm in multiple different directions and to rotate the C-arm about multiple different axes. The optical camera is configured to capture image data of a position of the C-arm relative to a location. The actions also include utilizing machine vision both to determine an initial position of the C-arm relative to the location and to navigate a return of the C-arm to the initial position when the C-arm has been moved from the initial position based on the image data.

In certain embodiments, the actions also include processing initial image data received from the optical camera to identify images features, to enhance the image features that were identified, and to utilize the image features that were enhanced as reference features for returning the C-arm to the initial position. The actions also include receiving an input from the user to activate utilization of the machine vision to navigate the return of the C-arm to the initial position. The actions also include processing live image data received from the optical camera to identify subsequent image features, to enhance the subsequent image features that were identified, and to compare the subsequent image features that were enhanced to the reference features.

FIG. 1 is a block diagram illustrating components of an example X-ray imaging system 100 (e.g., mobile X-ray imaging system). The mobile X-ray imaging system 100 includes an X-ray source 105 and an X-ray detector 107 mounted on a C-arm gantry 110 (e.g., C-arm).

The C-arm gantry 110 includes a C-arm motor 112 for adjusting the position of the C-arm gantry 110. More specifically, the C-arm gantry 110 is mechanically coupled to a C-arm carrier 111 (e.g., C-arm rotation device) which includes the C-arm motor 112, and the C-arm motor 112 may be driven to adjust the position of the C-arm gantry 110 with respect to the C-arm carrier 111. For example, the C-arm carrier 111 in conjunction with the C-arm motor 112 is configured to rotate the C-arm gantry 110 in an orbital direction relative to the C-arm carrier 111. In certain embodiments, the C-arm carrier 111 (via a motorized system) is configured to rotate a pivot (e.g., pivot point) where the C-arm carrier 111 is coupled to a mobile base 140 (e.g. automated guided vehicle) or an end of an L-arm coupled to the mobile base 140. The C-arm carrier 111 rotates about a rotational axis (e.g., horizontal axis) of the pivot. In certain embodiments having an L-arm, L-arm may rotate about a location where the other of the L-arm (i.e., the end of the L-arm not connected to the pivot) is coupled to the mobile base 140.

The mobile X-ray imaging system 100 also includes the mobile base 140. The C-arm carrier 111 is coupled to the mobile base 140. The mobile base 140 is configured to move (e.g., translocate) the mobile X-ray imaging system 100 from one location to another location on a floor. The mobile base 140 includes a chassis 141. The mobile base 140 includes one or more motors 142 for driving one or more wheels 144 (e.g. drive wheels) to adjust a position of the mobile base 140. In addition, one or more of the wheels 144 may be free or un-motorized.

The mobile X-ray imaging system 100 further includes a controller 150 including a processor 152 and a non-transitory memory 154. A method for controlling the mobile X-ray imaging system 100 may be stored as executable instructions 155 in the non-transitory memory 154 and executed by the processor 152.

The mobile X-ray imaging system 100 further includes a user interface 160 for receiving input from a user or operator of the mobile X-ray imaging system 100. The user interface 160 may be communicatively coupled to the controller 150 for providing commands input by a user via the user interface 160 to the controller 150. The user interface 160 may include one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as an interactive display device (e.g., touchscreen). In some examples the user interface 160 may be remotely located relative to the mobile X-ray imaging system 100. For example, the user interface 160 may be communicatively coupled to the controller 150 and/or the mobile X-ray imaging system 100, via a wired or wireless connection, and may be positioned away from the mobile base 140.

As an example, the memory 154 may store processor-executable software code or instructions (e.g., firmware or software), which are tangibly stored on a non-transitory computer readable medium. Additionally or alternatively, the memory 154 may store data. As an example, the memory 154 may include a volatile memory, such as random-access memory (RAM), and/or a nonvolatile memory, such as read-only memory (ROM), flash memory, a hard drive, or any other suitable optical, magnetic, or solid-state storage medium, or a combination thereof. Furthermore, the processor 152 may include multiple microprocessors, one or more "general-purpose" microprocessors, one or more special-purpose microprocessors, and/or one or more application specific integrated circuits (ASICS), or some combination thereof. For example, the processor 152 may include one or more reduced instruction set (RISC) or complex instruction set (CISC) processors. The processor 152 may include multiple processors, and/or the memory 154 may include multiple memory devices.

The mobile X-ray imaging system 100 includes an optical camera 162 (e.g., depth camera). The optical camera 162 is configured to acquire image data (e.g., video images including color images (red green blue (RGB) images) and depth images representing three-dimensional (3D) positional information of the surfaces within the image). The optical camera 162 is configured to capture image data of a position of the C-arm gantry 110 relative to a location (e.g., table supporting subject to be imaged). In certain embodiments, the optical camera 162 is mounted on the C-arm gantry 110. In certain embodiments, the optical camera 162 is mounted on the X-ray detector 107. In certain embodiments, the optical camera 162 is mounted on the X-ray source 105. In certain embodiments, the optical camera 162 may be mounted at an alternative position in the mobile X-ray imaging system 100. In certain embodiments, the optical camera 162 is separate from the mobile X-ray imaging system 100 (i.e., not mounted on the C-arm gantry). For example, the optical camera 162 may be mounted on a ceiling in a room where the mobile X-ray imaging system 100 is located.

In certain embodiments, the mobile X-ray imaging system 100 includes markers 164 (e.g., fiducial markers). The markers 164 are known (i.e., location of marker 164 is known). One or more markers 164 may be disposed on a table where the subject to be imaged is located, within the environment where the imaging is occurring (e.g., on objects within environment, on walls, on the floor, etc.), and/or on one or more components of the mobile X-ray imaging system 100. In certain embodiments, the markers 164 are fiducial patterns configured to be quickly located by computer vision systems when in the field of view of the optical camera 162. Image data with the markers 164 can be processed by the processor 152 to provide system positional information relative to the marker location. The markers 164 may be ArUco markers, ArTag markers, and/or AprilTag markers.

The mobile X-ray imaging system 100 includes C-arm position sensors 166. The C-arm position sensors 166 are disposed on various components of the mobile X-ray imaging system 100 (e.g., C-arm gantry 110, lift column, cross arm, etc.) are configured to detect motion of the C-arm gantry 110 and to track movement of the C-arm gantry 110. For example, the C-arm positions sensors 166 may track the lift column, cross arm, orbital rotation of the C-arm gantry 110, and/or lateral rotation of the C-arm gantry 110.

The mobile X-ray imaging system 100 include inertial measurement units 168. The inertial measurement units 168 may be disposed on various components of the mobile X-ray imaging system 100. The inertial measurement units 168 may be utilized to monitor the pose and movements of the C-arm gantry 110. The inertial measurement units 168 may include gyroscopes and/or accelerometers.

The controller 150 is configured to receive the image data (e.g., RGB images and/or depth images) from the optical camera 162 and to utilize machine-vision both to determine an initial position of the C-arm gantry 110 relative to the location (e.g., table having subject on it during intraoperative procedure) and to navigate a return of the C-arm gantry 110 to the initial position when the C-arm gantry 110 has been moved from the initial position based on the image data. The controller 150 is also configured to process initial image data received from the optical camera 162 to identify images features, to enhance the image features that were identified, and to utilize the image features that were enhanced as reference features for returning the C-arm gantry 110 to the initial position. In certain embodiments, the controller 150 is configured to utilize the one or more known markers 164 within the image data to determine respective positions of the X-ray imaging system 100 and the C-arm gantry 110 relative to locations of the one or more known markers 164.

The controller 150 is also configured to receive an input from the user (e.g., via the user interface 160) to activate utilization of the machine vision to navigate the return of the C-arm gantry 110 to the initial position. The controller 150 is also configured to process live image data received from the optical camera to identify subsequent image features, to enhance the subsequent image features that were identified, and to compare the subsequent image features that were enhanced to the reference features.

In certain embodiments, the controller 150 is configured to cause display, on a display (e.g., display device 165), of both the live image data along with user-perceptible instructions for navigating the C-arm gantry 110 back to the initial position based on the comparison of the subsequent image features that were enhanced to the reference features. In certain embodiments, the user-perceptible instructions include a direction of movement, a distance to a target, or a combination thereof. In certain embodiments, the controller 150 is configured to cause display, on the display, of both the live image data along with a reference image with the reference features to assist a user in navigating the C-arm gantry 110 back to the initial position. In certain embodiments, the controller 150 is configured to cause display, on the display, of the live image data, user-perceptible instructions for navigating the C-arm gantry 110 back to the initial position based on comparison of the subsequent image features that were enhanced to the reference features, and a reference image with the reference features to assist a user in navigating the C-arm gantry 110 back to the initial position.

In certain embodiments, the controller 150 is configured to provide control signals to move (e.g., automatically) the C-arm gantry 110 and/or the X-ray imaging system 100 to the initial position based on the comparison of the subsequent image features that were enhanced to the reference features. In certain embodiments, the initial image data and the live image data include red green blue images and/or depth images. In certain embodiments, the image features and the subsequent image features include shape edges, significantly bright or dark areas, unique shapes or objects, and/or contrast information.

In certain embodiments, the controller 150 is configured, during movement of the X-ray imaging system via the mobile base 140 from the initial position, to calculate a global localization of the C-arm gantry 110 and to map an environment based on the image data to form a trajectory relative to a floor that the mobile base 140 is located on, and to utilize the trajectory in navigating the return of the C-arm gantry 110 to the initial position. In certain embodiments, the controller 150 is configured to receive feedback from the sensors 166 and/or the inertial measurement units 168 to determine a position and movement of the C-arm gantry 110 and to estimate movement of the mobile base 140.

The controller 150 is further communicatively coupled to a display device 165 for displaying one or more X-ray images acquired via the X-ray detector 107. Further, in some examples, one or more of the controller 150, the user interface 160, and the display device 165 may be positioned away from (e.g., remotely from) the remaining components of the mobile X-ray imaging system 100.

Figure 2:
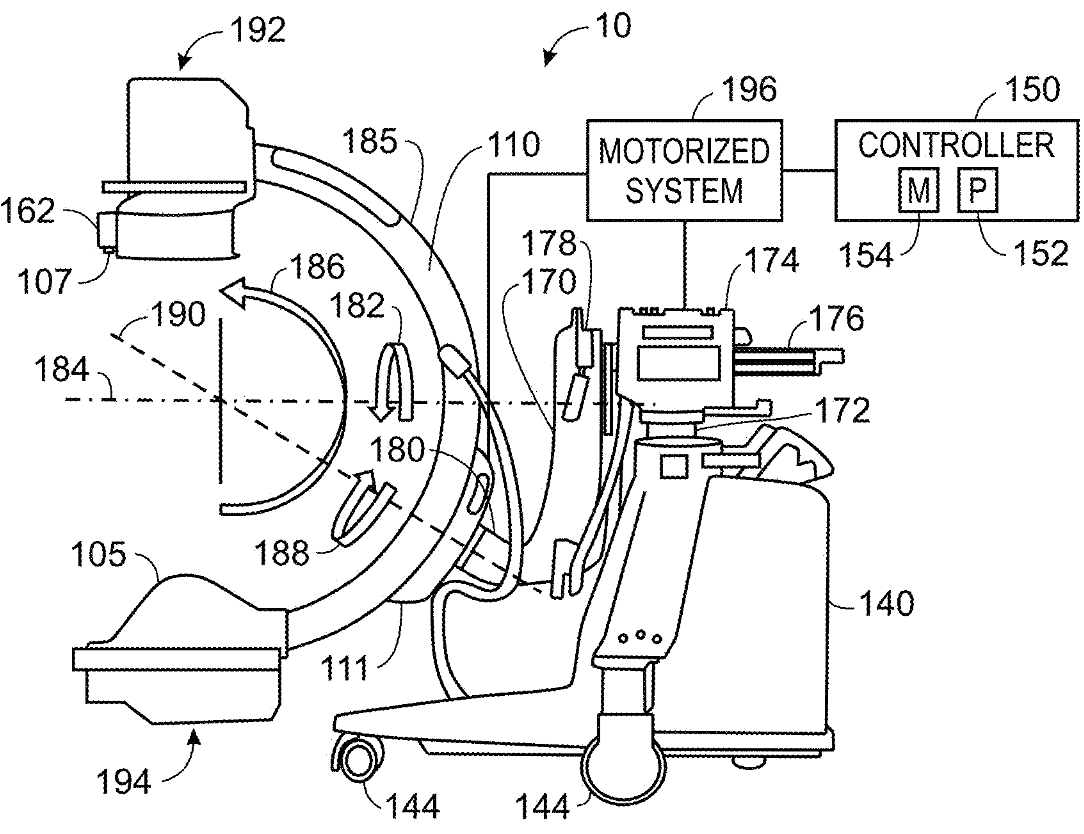
FIG. 2 is a schematic diagram of an embodiment of the X-ray imaging system in FIG. 1, in accordance with aspects of the present disclosure.

FIG. 2 is a schematic diagram of an embodiment of the X-ray imaging system 100 in FIG. 1. The X-ray imaging system 100 is configured to translate the C-arm gantry 110 in multiple different directions and to rotate the C-arm gantry 110 about multiple different axes. Although a mobile imaging system is illustrated, the embodiments described below may be utilized with any X-ray imaging system having a C-arm (e.g., a fixed imaging system). The X-ray imaging system 100 may utilize multiple imaging modalities (e.g., fluoroscopy, computed tomography, tomosynthesis, radiographic, magnetic resonance imaging, etc.) to acquire two-dimensional 2D and/or 3D image data. The X-ray imaging system 100 may be utilized for both diagnostic and interventional imaging. In addition, the X-ray imaging system 100 may be utilized for general purposes (e.g., general radiology, orthopedics, etc.) and special purposes (e.g., image guided surgery).

A principal function of the mobile X-ray imaging system 100 is to generate X-rays for diagnostic and interventional imaging. The X-ray imaging system 100 includes a support structure or base 140 (e.g., mobile base), the C-arm gantry 110, an L-arm 170, and the controller 150. The base 140 provides support for the C-arm gantry 110 and holds the C-arm gantry 110 in a suspended position. The lower portion of the base 140 includes wheels or casters 144 utilized to provide mobility to the system 100. The base 140 includes a vertical lift column 172 that permits the C-arm gantry 110 and L-arm 170 to move vertically in relation to base 140. Vertical lift column 172 terminates in an upper housing 174 of the base 140, wherein a horizontal extension arm 176 (e.g., cross arm) passes through upper housing 174 and permits L-arm 170 (as well as the C-arm gantry 110) to move perpendicularly in relation to vertical lift column 172 by movement (e.g., horizontal movement) of the horizontal extension arm 176 in relation to upper housing 174. The C-arm gantry 110 may be moved along the axis of the horizontal extension arm 176 to effect transverse tracking motion. The L-arm 170 is coupled to the horizontal extension arm 176 via end 178 and configured to pivot or rotate about the horizontal extension arm 176 such that the L-arm 170 can be made to pivot in a 360-degree arc. The horizontal extension arm 176 is coupled to one end 178 of the L-arm 170, while an outer end 180 of the L-arm 176 is coupled to C-arm gantry 110. Rotation of the L-arm 176 about where it is coupled to the horizontal extension arm 176 enables the C-arm gantry 110 to be rotated (e.g., 360 degrees) in a lateral direction 182 (e.g., circumferential direction) about a lateral axis 184 (e.g., parallel to the horizontal extension arm 176) relative to the base 140.

The C-arm gantry 110 is coupled to the C-arm carrier 111 that is coupled to the end 180 of the L-arm 170. The C-arm carrier 111 is coupled to an assembly of rollers or wheels (e.g., disposed within a track 185 of the C-arm gantry 110) that enables the C-arm gantry 110 to move or rotate about an orbital axis 186 in an orbital direction along the track 185 relative to C-arm carrier 111.

In certain embodiments, the C-arm carrier 111 also enables the C-arm gantry 110 to rotate (e.g., circumferentially) or flip-flop (e.g., as indicated by reference numeral 188) about an axis 190 (e.g., flip-flop axis) emanating from where the C-arm carrier 111 is coupled to the C-arm gantry 110 and, thus, the base 140. The C-arm carrier 111 enables 180 degrees of rotation of the C-arm gantry 110 relative to the C-arm carrier 111.

The X-ray detector 107 and the X-ray source 105 are coupled to opposing ends 192, 194 of the C-arm gantry 110 to form an image chain. The C-arm gantry 110 allows the X-ray detector 107 and the X-ray source 105 to be mounted and positioned about an object to be imaged, such as a patient. The C-arm gantry 110 may be a circular C-shaped or an arc-shaped member, for example. The C-arm gantry 110 enables selective positioning of the X-ray detector 107 and the X-ray source 105 with respect to the width and length of the patient or other object located within the interior free space of the C-arm gantry 110. The X-ray detector and the X-ray source 46 are used to generate a diagnostic image representative of the object being imaged.

Rotation about the axes 184, 186, 190 are independent (e.g., separate or different from each other). Rotation of the C-arm gantry 110 with respect to these axes 184, 186, 190 is driven by a motorized system 196. The motorized system 196 may include one or more motors or servomotors to drive the rotation about these axes 184, 186, 190 via automation. The motors or servomotors may be disposed throughout different components of the imaging system 100. The motorized system 196 may be coupled to control system or controller 150 (e.g., disposed within the base 140 and/or remote from the imaging system 100). The controller 150 include the memory 154 and one or more processors 152 to execute code or instructions stored within the memory 154. The controller 150 may control the automated movement of the C-arm gantry 110 about the axes 184, 186, 190. As depicted in FIG. 2, the optical camera 162 is mounted on the C-arm gantry 110. In particular, the optical camera 162 is mounted on the X-ray detector 107.

Figure 3:
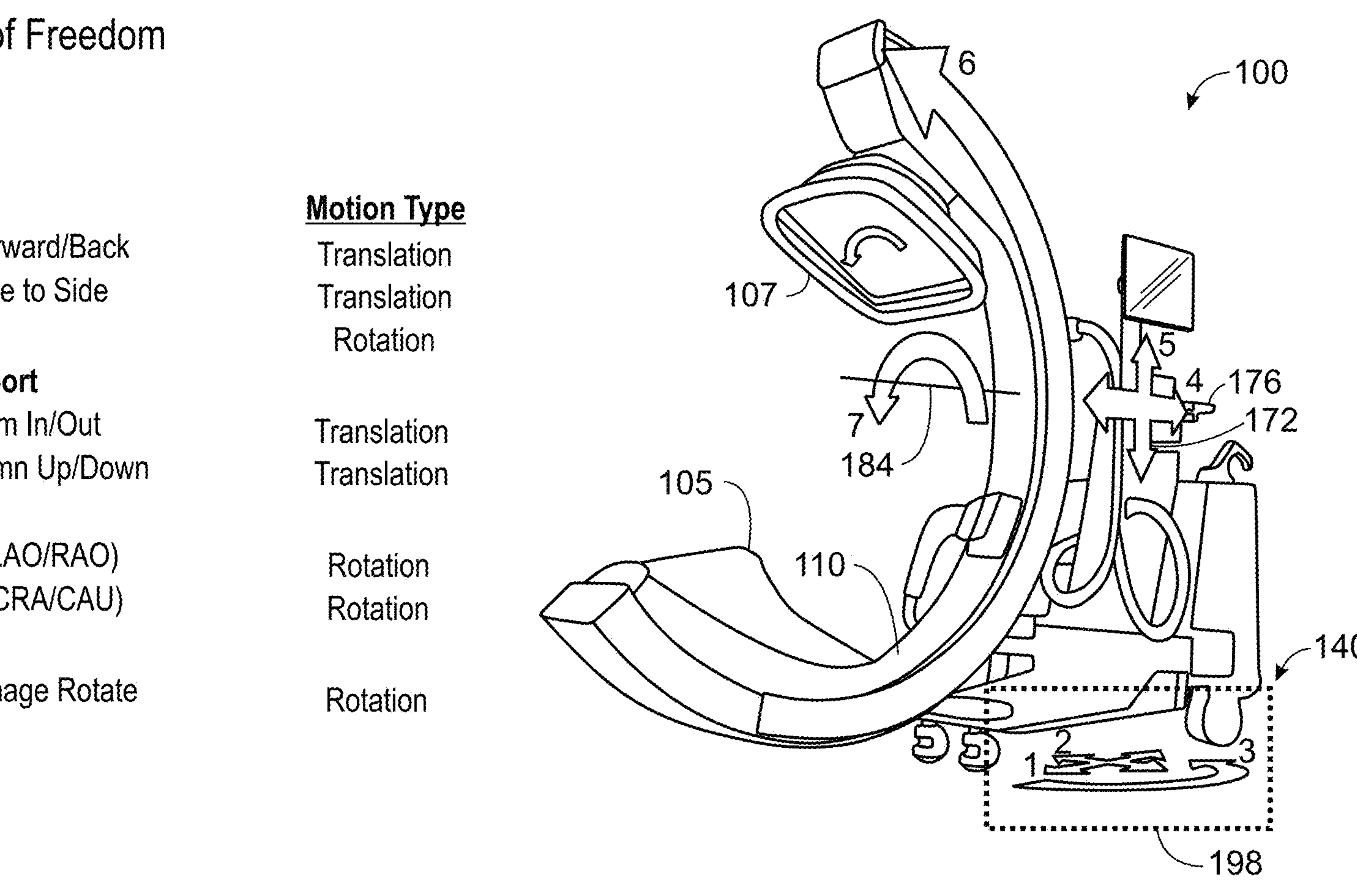
FIG. 3 is a schematic diagram of the X-ray imaging system in FIG. 1 illustrating the degrees of freedom in movement relevant to a position of a C-arm gantry, in accordance with aspects of the present disclosure.

FIG. 3 is a schematic diagram of the X-ray imaging system 100 in FIG. 1 illustrating the degrees of freedom in movement relevant to a position of the C-arm gantry 110. The first, second, and third degrees occur along the floor as indicated by box 198. The techniques described herein estimate these degrees of movement since there are no sensors associated with these types of movement on the mobile base 140. The first degree of freedom relates to forward and backward movement (i.e., translation) (as indicated by arrow 1) of the X-ray imaging 100 along the floor via the mobile base 140 that affects the positioning of C-arm gantry 110. The second degree of freedom relates to side-to-side movement (i.e., translation) (as indicated by arrow 2) of the X-ray imaging 100 along the floor via the mobile base 140 that affects the positioning of C-arm gantry 110. The third degree of freedom relates to steering (i.e., rotation) (as indicated by arrow 3) of the X-ray imaging 100 about a location on the floor via the mobile base 140 that affects the positioning of C-arm gantry 110.

The fourth and fifth degrees of freedom relate to movement of the gantry support that moves the C-arm gantry 110. The fourth degree of freedom relates to in and out motion (i.e., translation) of the cross-arm 176 (e.g., horizontal extension arm) as indicated by arrow 4. The fifth degree of freedom relates to up and down motion (i.e., translation) of the vertical lift column 172 as indicated by arrow 5.

The sixth and seventh degrees of freedom relate to movement of the C-arm gantry 110. The sixth degree of freedom relates to the orbital rotation (e.g., left anterior oblique (LAO) rotation and right anterior oblique (RAO) rotation) of the C-arm gantry 110 as indicated by arrow 6. The seventh degree of freedom relates to the lateral rotation (e.g., cranial (CRA) rotation and caudal (CAU) rotation) of the C-arm gantry 110 about lateral axis 184 as indicated by arrow 7.

The eight degree of freedom relates to the X-ray detector 107. The X-ray detector 107 may be rotated as indicated by arrow 8.

Figure 4:
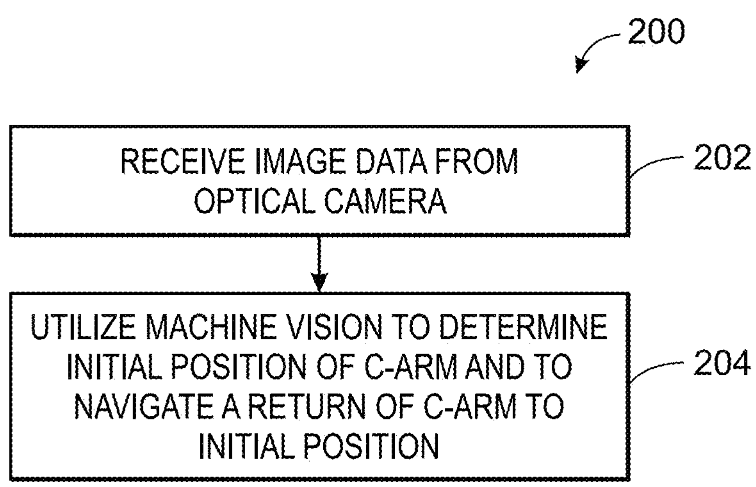
FIG. 4 is a flow chart of a method for utilizing fiducials detection for movement estimation and guidance, in accordance with aspects of the present disclosure.

FIG. 4 is a flow chart of a method 200 for utilizing fiducials detection for movement estimation and guidance. One or more steps of the method 200 may be performed by processing circuitry of the X-ray imaging system 100 in FIG. 1.

The method 200 includes receiving image data (e.g., input video) from an optical camera (e.g., mounted on a C-arm of an X-ray imaging system), wherein the optical camera is configured to capture image data of a position of the C-arm relative to a location (e.g., table having a subject being imaged and undergoing an intraoperative procedure) (block 202). The image data may include video including color images (e.g., RGB images) and/or depth images. The method 200 also includes utilizing machine vision (e.g., computer vision) both to determine an initial position of the C-arm relative to the location and to navigate a return of the C-arm to the initial position when the C-arm has been moved from the initial position based on the image data (block 204).

Figure 5A:
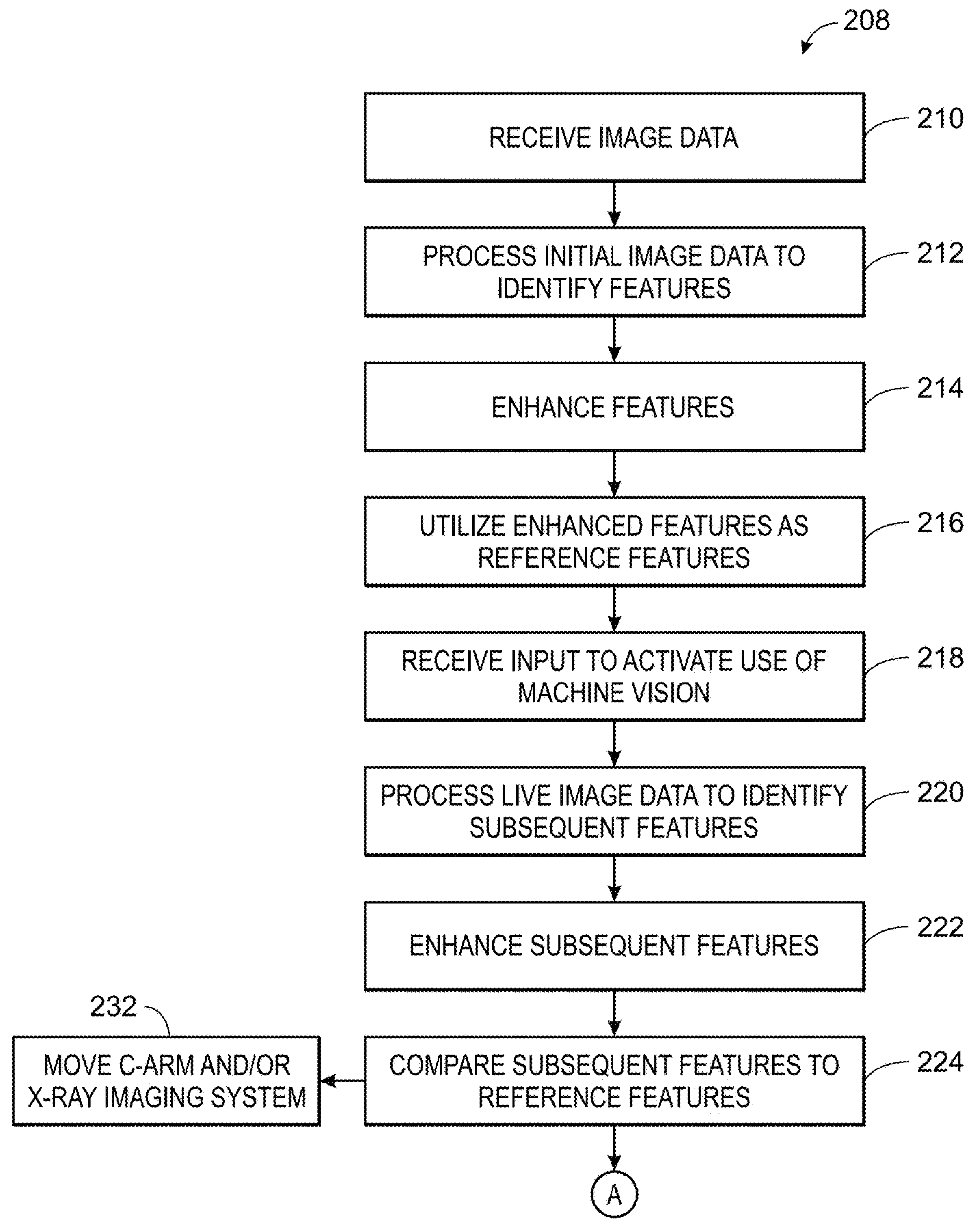
FIGS. 5A and 5B are a more detailed flow chart of a method for utilizing fiducials detection for movement estimation and guidance, in accordance with aspects of the present disclosure.
Figure 5B:
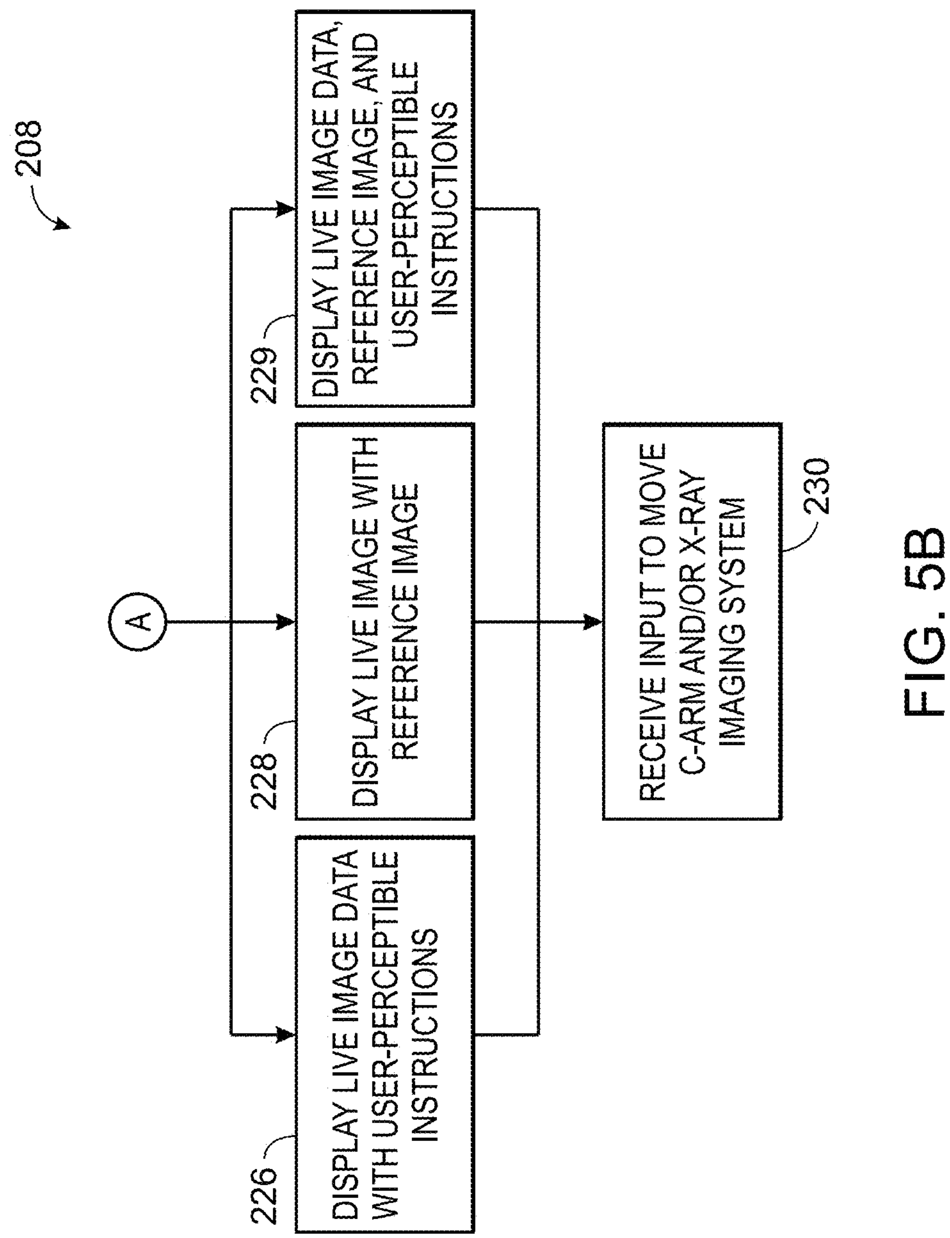

FIGS. 5A and 5B are a flow chart of method 208 for utilizing fiducials detection for movement estimation and guidance. One or more steps of the method 208 may be performed by processing circuitry of the X-ray imaging system 100 in FIG. 1.

The method 208 includes receiving image data (e.g., input video) from an optical camera (e.g., mounted on a C-arm of an X-ray imaging system), wherein the optical camera is configured to capture image data of a position of the C-arm relative to a location (e.g., table having a subject being imaged and undergoing an intraoperative procedure) (block 210). The image data may include video including color images (e.g., RGB images) and/or depth images.

The method 208 also includes processing initial image data (e.g., input video frame) received from the optical camera to identify images features of interest (block 212). Images features that may be identified include sharp edges, significantly bright or dark areas, unique shapes or objects, and/or contrast information. The images may be decomposed to individual colors, transformed to grayscale or other color spaces, smoothed, sharpened, or otherwise manipulated to facilitate feature extraction. The method 208 further includes enhance the image features that were identified to provide the best user display to facilitate the return of the C-arm to its initial position (block 214). The method 208 even further includes utilizing the image features that were enhanced as reference features for returning the C-arm to the initial position (block 216).

The method 208 further includes receiving an input from the user to activate utilization of the machine vision to navigate the return of the C-arm to the initial position (block 218). The method 208 even further includes processing live image data received from the optical camera to identify subsequent image features (block 220). The live mage data may include video including color images (e.g., RGB images) and/or depth images. The subsequent images features that may be identified include sharp edges, significantly bright or dark areas, unique shapes or objects, and/or contrast information. The images may be decomposed to individual colors, transformed to grayscale or other color spaces, smoothed, sharpened, or otherwise manipulated to facilitate feature extraction. The method 208 includes enhancing the subsequent image features that were identified (block 222). The method 208 includes comparing the subsequent image features that were enhanced to the reference features (block 224).

In certain embodiments, the method 208 further includes causing display, on a display, of both the live image data along with user-perceptible instructions for navigating the C-arm back to the initial position based on the comparison of the subsequent image features that were enhanced to the reference features (block 226). In certain embodiments, the method 208 further includes causing display, on the display, of both the live image data along with a reference image with the reference features to assist a user in navigating the C-arm back to the initial position (block 228). In certain embodiments, the method 208 further includes causing display, on the display, of the live image data, user-perceptible instructions for navigating the C-arm back to the initial position based on comparison of the subsequent image features that were enhanced to the reference features, and a reference image with the reference features to assist a user in navigating the C-arm back to the initial position (block 229). In certain embodiments, the user-perceptible instructions may be a direction of movement, a distance to a target, or a combination thereof. In certain embodiments, a user input may be received to turn the instructions and/or reference features on or off. In certain embodiments, the method 208 includes receiving an input from a user (e.g., via the user interface) to move the C-arm and/or X-ray imaging system to navigate the C-arm back to its initial position using the assistance provided (block 230). In certain embodiments, the method 208 includes providing control signals to move (e.g., in some embodiments automatically) the C-arm and/or the X-ray imaging system to the initial position based on the comparison of the subsequent image features that were enhanced to the reference features (block 232).

Figure 6:
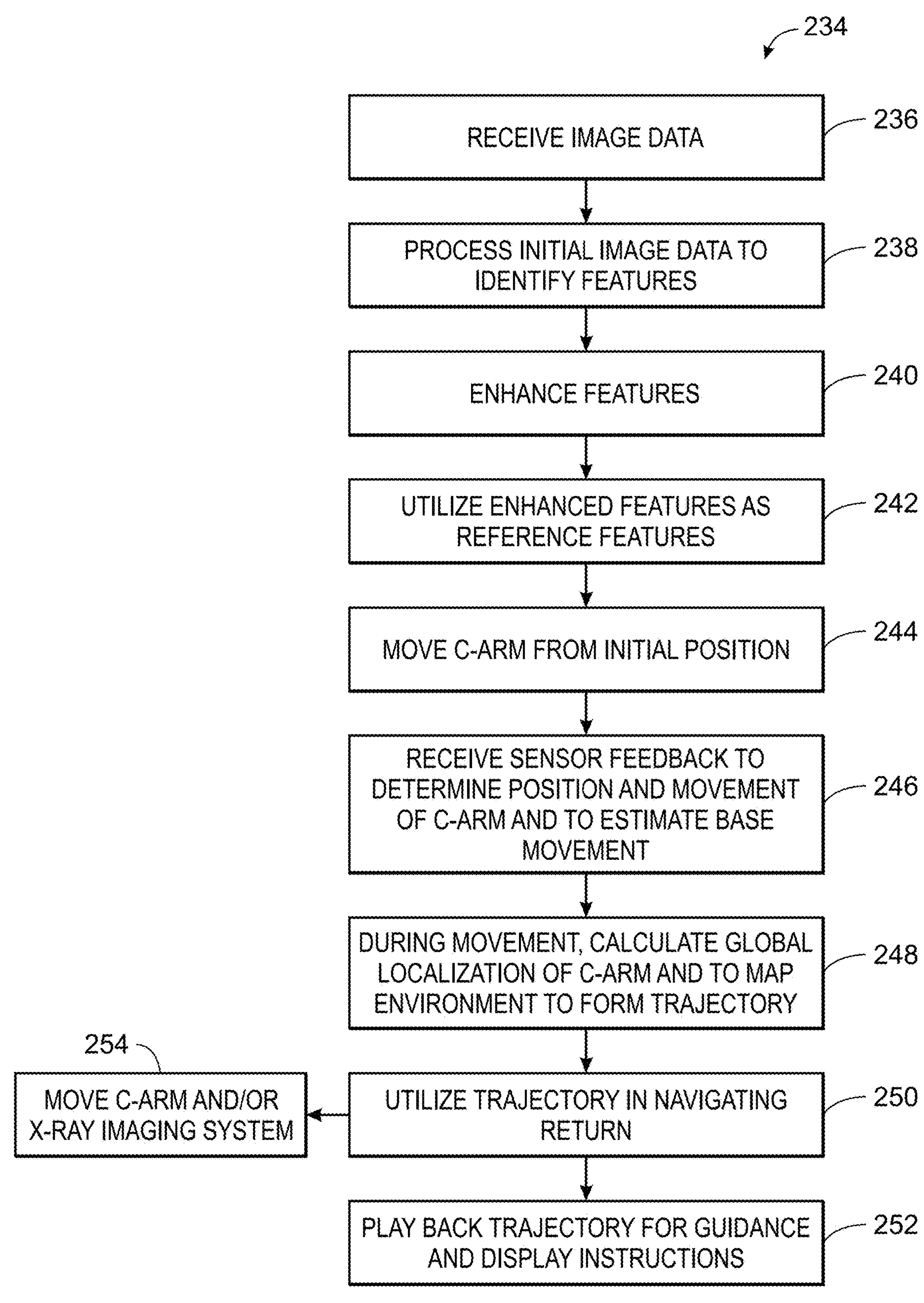
FIG. 6 is a more detailed flow chart of a method for utilizing fiducials detection for movement estimation and guidance (e.g., utilizing a trajectory), in accordance with aspects of the present disclosure.

FIG. 6 is a flow chart of method 234 for utilizing fiducials detection for movement estimation and guidance. One or more steps of the method 234 may be performed by processing circuitry of the X-ray imaging system 100 in FIG. 1.

The method 234 includes receiving image data (e.g., input video) from an optical camera (e.g., mounted on a C-arm of an X-ray imaging system), wherein the optical camera is configured to capture image data of a position of the C-arm relative to a location (e.g., table having a subject being imaged and undergoing an intraoperative procedure) (block 236). The image data may include video including color images (e.g., RGB images) and/or depth images.

The method 234 also includes processing initial image data (e.g., input video frame) received from the optical camera to identify images features of interest (block 238). In certain embodiments, the image features may be richer information such as contrast. In certain embodiments, the image features may be known markers disposed within a field of view of the optical camera. The one or more known markers within the image data may be utilized to determine respective positions of the X-ray imaging system and the C-arm relative to locations of the one or more known markers The method 234 further includes enhance the image features that were identified to provide the best user display to facilitate the return of the C-arm to its initial position (block 240). The method 234 even further includes utilizing the image features that were enhanced as reference features for returning the C-arm to the initial position (block 242). The method 234 utilizes computer vision for blocks 238-242.

The method 234 includes moving the C-arm from its initial position (block 244). Some of the movement of the C-arm may occur due to movement via the mobile base (e.g., translation and/or rotation). The method 234 includes receiving feedback from sensors disposed on components of the X-ray imaging system to determine a position and movement of the C-arm and to estimate movement of the mobile base (block 246). In certain embodiments, any known markers within the image data may also be utilized in determining a position and movement of the C-arm and to estimate movement of the mobile base.

The method 234 also includes, during movement of the X-ray imaging system via the mobile base from the initial position, calculating a global localization of the C-arm and to map an environment based on the image data to form a trajectory relative to a floor that the mobile base is located on (block 248). The method 234 further includes utilizing the trajectory in navigating the return of the C-arm to the initial position (block 250). In certain embodiments, utilizing the trajectory includes playing back (e.g., on a display) the trajectory for guidance while also displaying user-perceptible instructions to assist a user in navigating the C-arm back to the initial position (block 252). In certain embodiments, the method 234 includes providing control signals to move (e.g., in some embodiments automatically) the C-arm and/or the X-ray imaging system to the initial position based on the comparison of the subsequent image features that were enhanced to the reference features (block 254).

Figure 7:
FIG. 7 is a graphical user interface displayed on a display (e.g., with edge-enhanced image highlighting a section of interest), in accordance with aspects of the present disclosure.

FIG. 7 is a graphical user interface 256 displayed on a display 165 (e.g., with edge-enhanced image highlighting a section of interest). The graphical user interface 256 includes a graphic 258 indicating the current position of the C-arm relative to a table (e.g., that an object of interest is located). The graphical user interface 256 includes a reference image 260 (e.g., when the C-arm was in the initial position) that had been processed as described in the method 208 in FIGS. 5A and 5B and obtained from an optical camera (e.g., mounted on a detector on the C-arm). The graphical user interface 256 also discloses a live image 262 from the optical camera that has been processed as described in the method 208 in FIGS. 5A and 5B. In particular, the edges have been enhanced (e.g., highlighted) for a section of interest within the camera field of view. The section of interest is a drape disposed over a phantom on a table. The graphical user interface 256 also includes a graphic 264 that includes positional information for the C-arm (e.g., position relative to 90 degrees LAO and 0 degrees CRA). The highlighted edges and the reference image 260 are utilized to provide the user assistance in returning the C-arm to its initial position.

Figure 8:
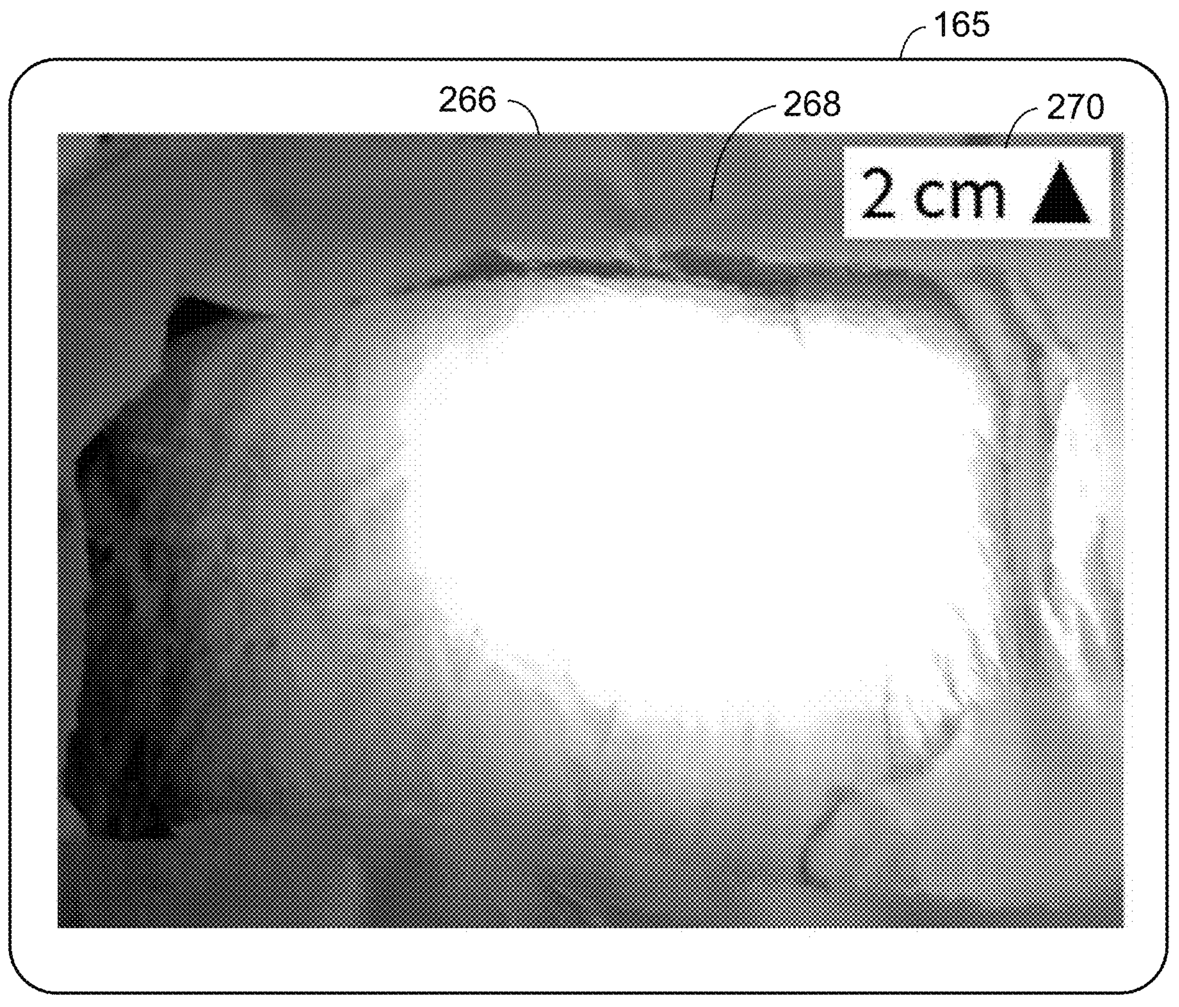
FIG. 8 is a graphical user interface displayed on a display (e.g., with user-perceptible instructions), in accordance with aspects of the present disclosure.

FIG. 8 is a graphical user interface 266 displayed on the display 165 (e.g., with user-perceptible instructions). The graphical user interface 266 also discloses a live image 268 obtained from an optical camera (e.g., mounted on a detector on the C-arm) that has been processed as described in the method 208 in FIG. 5. The graphical user interface 266 includes a user-perceptible directions 270 to provide the user assistance in returning the C-arm to its initial position. The object within the camera field of view is a drape disposed over a phantom on a table.

Figure 9:
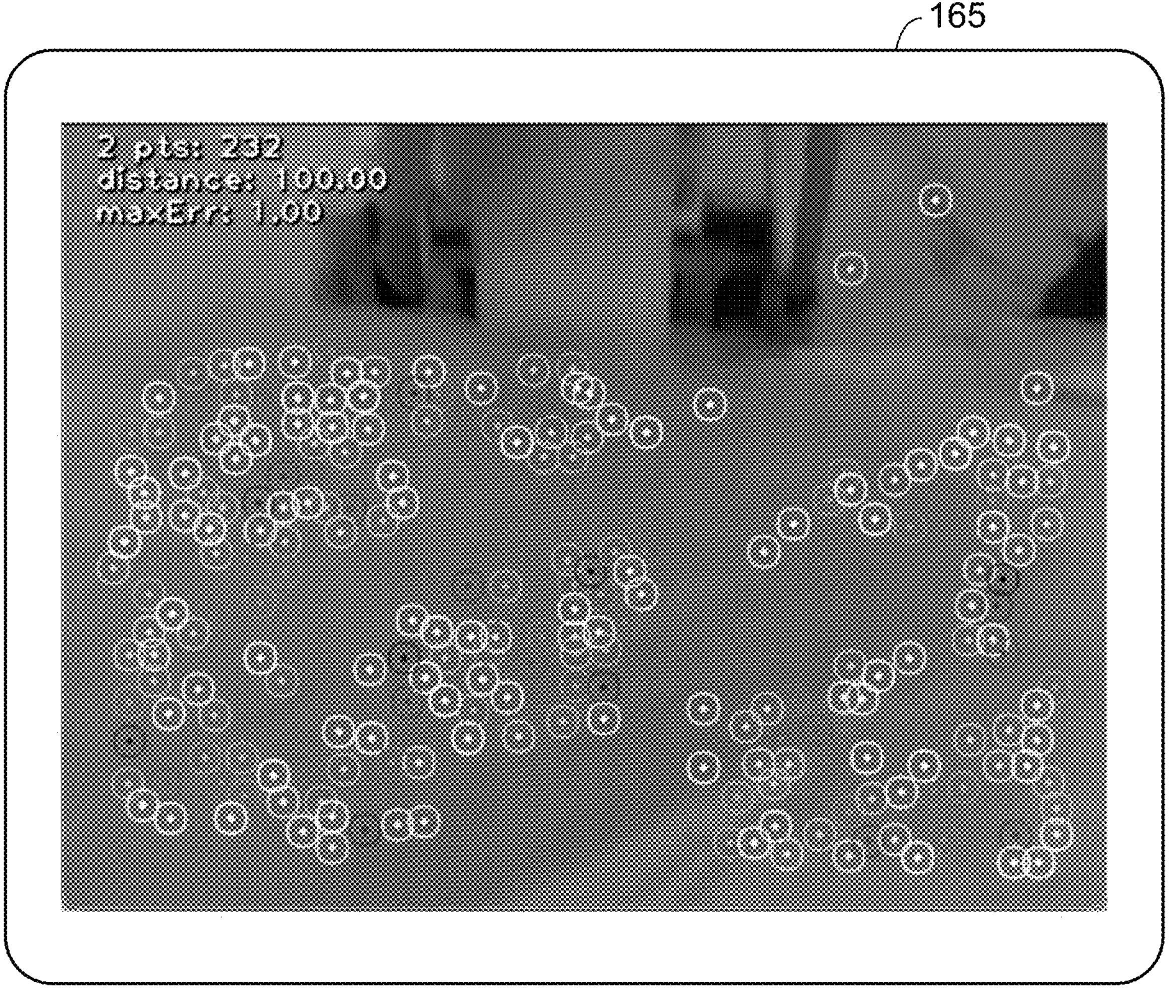
FIG. 9 is a graphical user interface illustrating extraction of information (e.g., image features such as contrast) from image data, in accordance with aspects of the present disclosure.

FIG. 9 is a graphical user interface 272 illustrating extraction of information (e.g., image features such as contrast) from image data. The graphical user interface 272 also discloses a live image 274 obtained from an optical camera (e.g., mounted on a detector on the C-arm). As depicted, machine vision is utilized to extract and to utilize contrast information from different points of the image. The analysis of the contrast image is not displayed to a user.

Figure 10:
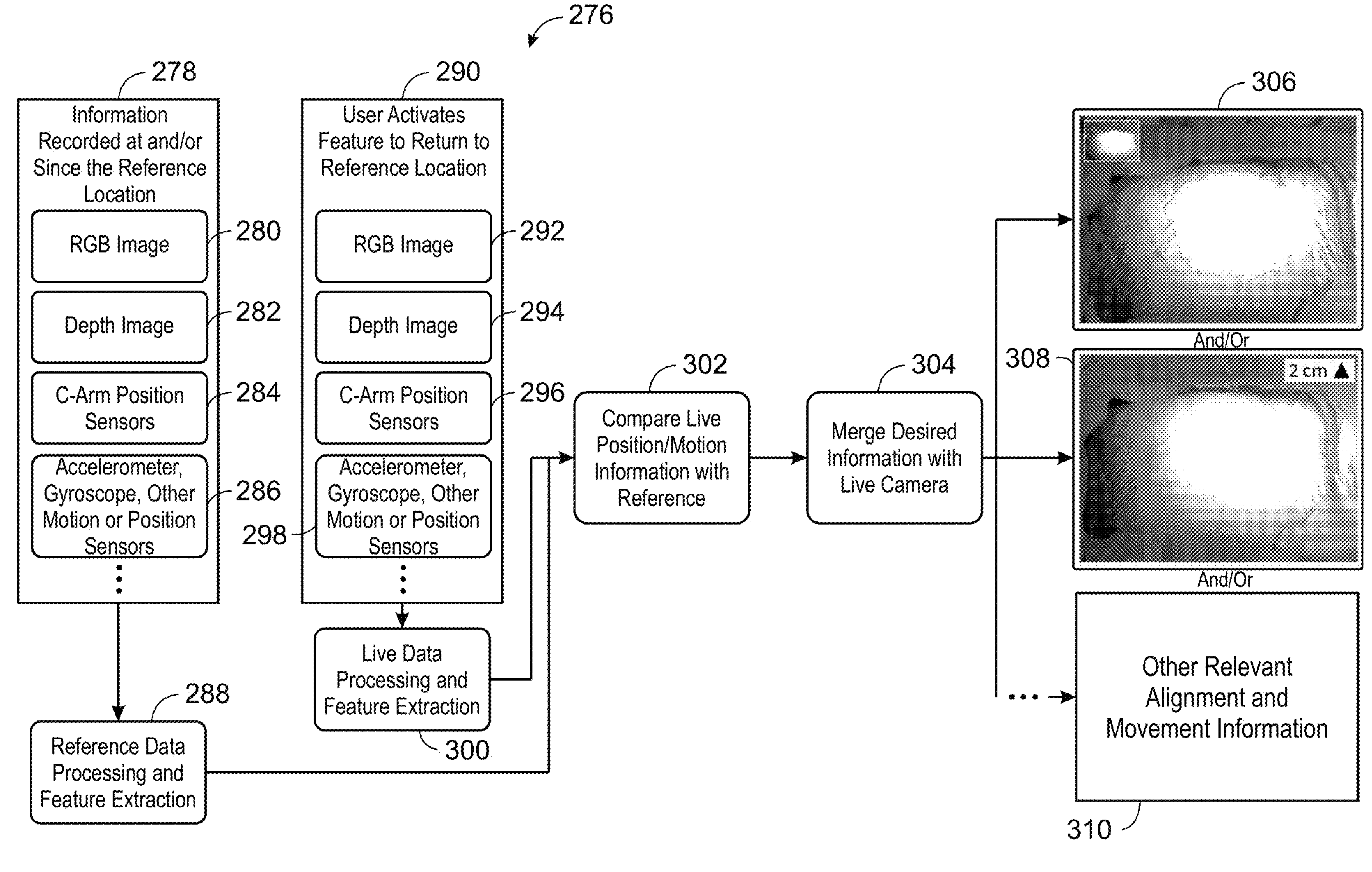
FIG. 10 is a schematic diagram of a process for utilizing fiducials detection for movement estimation and guidance, in accordance with aspects of the present disclosure.

FIG. 10 is a schematic diagram of a process 276 for utilizing fiducials detection for movement estimation and guidance. The process 276 includes recording information at or since the C-arm was at a reference location or position (block 278). The information may include RGB images 280 and depth images 282 from an optical camera (e.g., mounted on the C-arm). The information may also include feedback 284 from C-arm positions sensors disposed on various components of the X-ray imaging system. The information may also include feedback 286 from accelerometers, gyroscopes, and/or other motion or position sensors. The feedback 284, 286 provides information on the position (e.g., pose) and/or position of the C-arm. The reference information or data is then processed and feature extraction performed as described above (block 288).

The process 276 includes, upon user activation, obtaining live information for utilization (via machine vision) to return the C-arm to its reference location or position (block 290). The live information may include RGB images 292 and depth images 294 from an optical camera (e.g., mounted on the C-arm). The live information may also include feedback 296 from C-arm positions sensors disposed on various components of the X-ray imaging system. The live information may also include feedback 298 from accelerometers, gyroscopes, and/or other motion or position sensors. The feedback 296, 298 provides information on the position (e.g., pose) and/or position of the C-arm. The live information or data is then processed and feature extraction performed as described above (block 300).

The process 276 includes comparing live position/motion information with the reference information (block 302). The process 276 also includes merging desired information with the feed from the live optical camera (block 304). In certain embodiments, the process 276 includes displaying a reference image and highlighting features (e.g., edges) seen within the live feed as shown in graphical user interface 306. In certain embodiments, the process 276 includes displaying the live feed along with user-perceptible instructions (e.g., distance and direction) to assist the user in moving the C-arm as shown in graphical user interface 308. In certain embodiments, the process 276 includes displaying other relevant alignment and movement information as indicated by reference numeral 310.

Technical effects of the disclosed embodiments include providing an easier and clearer way to return the C-arm to a previous (e.g., initial) position. Technical effects of the disclosed embodiments providing user instructions for the trajectory needed to be taken to return the C-arm to the previous position including, but not limited, to visual clues about where to go, how far, and what to check for correctness. These user aids can streamline the return to the same position workflow. Technical effects of the disclosed embodiments include utilizing the disclosed techniques to virtually move an X-ray image to be virtually moved as the C-arm changes position to show the approximate place for the next X-ray shot. Technical effects of the disclosed embodiments include eliminating the need for fluoro-hunting.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:

an X-ray radiation source;

an X-ray detector; and a C-arm having the X-ray radiation source disposed on a first end and the X-ray detector disposed on a second end opposite the first end, wherein the X-ray imaging system is configured to translate the C-arm in multiple different directions and to rotate the C-arm about multiple different axes;

an optical camera configured to capture image data of a position of the C-arm relative to a location; and a controller comprising a memory and a processing system comprising one or more processors, and the controller is configured to receive the image data from the optical camera and to utilize machine vision both to determine an initial position of the C-arm relative to the location and to navigate a return of the C-arm to the initial position when the C-arm has been moved from the initial position based on the image data.

2. The X-ray imaging system of claim 1, wherein the optical camera is mounted on the C-arm.

3. The X-ray imaging system of claim 1, wherein the controller is configured to process initial image data received from the optical camera to identify images features, to enhance the image features that were identified, and to utilize the image features that were enhanced as reference features for returning the C-arm to the initial position.

4. The X-ray imaging system of claim 3, wherein the controller is configured to receive an input from a user to activate utilization of the machine vision to navigate the return of the C-arm to the initial position.

5. The X-ray imaging system of claim 4, wherein the controller is configured to process live image data received from the optical camera to identify subsequent image features, to enhance the subsequent image features that were identified, and to compare the subsequent image features that were enhanced to the reference features.

6. The X-ray imaging system of claim 5, further comprising a display, and wherein the controller is configured to cause display, on the display, of both the live image data along with user-perceptible instructions for navigating the C-arm back to the initial position based on the comparison of the subsequent image features that were enhanced to the reference features.

7. The X-ray imaging system of claim 6, wherein the user-perceptible instructions comprise a direction of movement, a distance to a target, or a combination thereof.

8. The X-ray imaging system of claim 5, further comprising a display, and wherein the controller is configured to cause display, on the display, of both the live image data along with a reference image with the reference features to assist a user in navigating the C-arm back to the initial position.

9. The X-ray imaging system claim 5, further comprising a display, and wherein the controller is configured to cause display, on the display, of the live image data, user-perceptible instructions for navigating the C-arm back to the initial position based on comparison of the subsequent image features that were enhanced to the reference features, and a reference image with the reference features to assist a user in navigating the C-arm back to the initial position.

10. The X-ray imaging system of claim 5, wherein the controller is configured to provide control signals to move the C-arm and/or the X-ray imaging system to the initial position based on the comparison of the subsequent image features that were enhanced to the reference features.

11. The X-ray imaging system of claim 5, wherein the initial image data and the live image data comprise red green blue images and/or depth images.

12. The X-ray imaging system of claim 5, wherein the image features and the subsequent image features comprise sharp edges, significantly bright or dark areas, unique shapes or objects, and/or contrast information.

13. The X-ray imaging system of claim 5, further comprising a mobile base configured to move the X-ray imaging system, and wherein the controller is configured, during movement of the X-ray imaging system via the mobile base from the initial position, to calculate a global localization of the C-arm and to map an environment based on the image data to form a trajectory relative to a floor that the mobile base is located on, and to utilize the trajectory in navigating the return of the C-arm to the initial position.

14. The X-ray imaging system of claim 13, further comprising sensors disposed on components of the X-ray imaging system to determine a position and movement of the C-arm, and wherein the controller is configured to receive feedback from the sensors to determine a position and movement of the C-arm and to estimate movement of the mobile base.

15. The X-ray imaging system of claim 14, wherein the sensors comprise one or more of a C-arm position sensor, an accelerometer, and a gyroscope.

16. The X-ray imaging system of claim 15, further comprising one or more known markers disposed within a field of view of the optical camera, and wherein the controller is configured to utilize the one or more known markers within the image data to determine respective positions of the X-ray imaging system and the C-arm relative to locations of the one or more known markers.

17. A computer-implemented method, comprising:

receiving, at a processing system comprising one or more processors, image data from an optical camera mounted on a C-arm of an X-ray imaging system, wherein the X-ray imaging system comprises an X-ray radiation source, an X-ray detector, and the C-arm having the X-ray radiation source disposed on a first end and the X-ray detector disposed on a second end opposite the first end, wherein the X-ray imaging system is configured to translate the C-arm in multiple different directions and to rotate the C-arm about multiple different axes, and wherein the optical camera is configured to capture image data of a position of the C-arm relative to a location; and utilizing, via the processing system, machine vision both to determine an initial position of the C-arm relative to the location and to navigate a return of the C-arm to the initial position when the C-arm has been moved from the initial position based on the image data.

18. The computer-implemented method of claim 17, further comprising:

processing, via the processing system, initial image data received from the optical camera to identify images features, to enhance the image features that were identified, and to utilize the image features that were enhanced as reference features for returning the C-arm to the initial position;

receiving, at the processing system, an input from a user to activate utilization of the machine vision to navigate the return of the C-arm to the initial position; and processing, via the processing system, live image data received from the optical camera to identify subsequent image features, to enhance the subsequent image features that were identified, and to compare the subsequent image features that were enhanced to the reference features.

19. A non-transitory computer-readable medium, the computer-readable medium comprising processor-executable code that when executed by a processing system comprising one or more processors, causes the processing system to:

receive image data from an optical camera mounted on a C-arm of an X-ray imaging system, wherein the X-ray imaging system comprises an X-ray radiation source, an X-ray detector, and the C-arm having the X-ray radiation source disposed on a first end and the X-ray detector disposed on a second end opposite the first end, wherein the X-ray imaging system is configured to translate the C-arm in multiple different directions and to rotate the C-arm about multiple different axes, and wherein the optical camera is configured to capture image data of a position of the C-arm relative to a location; and utilize machine vision both to determine an initial position of the C-arm relative to the location and to navigate a return of the C-arm to the initial position when the C-arm has been moved from the initial position based on the image data.

20. The non-transitory computer-readable medium of claim 19, wherein the processor-executable code, when executed by the processing system, further causes the processing system to:

process initial image data received from the optical camera to identify images features, to enhance the image features that were identified, and to utilize the image features that were enhanced as reference features for returning the C-arm to the initial position;

receive an input from a user to activate utilization of the machine vision to navigate the return of the C-arm to the initial position; and process live image data received from the optical camera to identify subsequent image features, to enhance the subsequent image features that were identified, and to compare the subsequent image features that were enhanced to the reference features.

* * * * *